(12) United States Patent
Shi (10) Patent No.: US 10,820,848 B2
(45) Date of Patent: Nov. 3, 2020

(54) DISPOSAL PUNCTURE DEPTH ADJUSTABLE SAFETY LANCET

(71) Applicant: STERILANCE MEDICAL (SUZHOU) INC., Jiangsu (CN)

(72) Inventor: Guoping Shi, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 161 days.

(21) Appl. No.: 16/087,154

(22) PCT Filed: Mar. 21, 2017

(86) PCT No.: PCT/CN2017/077518
§ 371 (c)(1),
(2) Date: Sep. 21, 2018

(87) PCT Pub. No.: WO2017/162141
PCT Pub. Date: Sep. 28, 2017

(65) Prior Publication Data
US 2019/0053746 A1    Feb. 21, 2019

(30) Foreign Application Priority Data

Mar. 21, 2016 (CN) .......................... 2016 1 0158481

(51) Int. Cl.
*A61B 5/151*       (2006.01)
(52) U.S. Cl.
CPC .......... *A61B 5/15186* (2013.01); *A61B 5/151* (2013.01); *A61B 5/15107* (2013.01); *A61B 5/15142* (2013.01)
(58) Field of Classification Search
CPC ....... A61B 5/15; A61B 5/151; A61B 5/15107; A61B 5/15142; A61B 5/15186;
(Continued)

(56) References Cited

U.S. PATENT DOCUMENTS 5,730,753 A * 3/1998 Morita ............. A61B 5/150022
                                                      600/583
6,852,119 B1 * 2/2005 Abulhaj ........... A61B 5/150022
                                                      606/172
(Continued)

FOREIGN PATENT DOCUMENTS

CN        200945164 Y     9/2007
CN        201505140 U     6/2010
(Continued)

OTHER PUBLICATIONS

Jun. 21, 2017 International Search Report issued in International Patent Application No. PCT/CN2017/077518.

*Primary Examiner* — Katherine H Schwiker
*Assistant Examiner* — Alexis D Amechi
(74) *Attorney, Agent, or Firm* — Oliff PLC (57) ABSTRACT

An improved disposable puncture depth adjustable safety lancet includes a shell, a lancet core, a spring, and a trigger. The shell has an adjusting ring at a front end thereof to adjust a puncture depth, the adjusting ring being sleeved and clearance-fit at an outside of the trigger head. The adjusting ring and the shell are rotationally connected in a peripheral direction and are fixedly connected in an axial direction, and a rotational locating structure is formed by the adjusting ring and the shell in the peripheral direction. The adjusting ring has an inner wall equipped with a rotating step face or rotating bevel, and rotating the adjusting ring locates the adjusting ring in different locating positions. The rotating step face or rotating bevel is configured to meet the collision face of the lancet core in different axial positions, thereby changing the puncture depth of needle tip.

9 Claims, 7 Drawing Sheets (58) Field of Classification Search
CPC ........ A61B 5/150183; A61B 5/150412; A61B 5/150022; A61B 5/15117; A61B 5/15109; A61B 5/15111; A61B 5/15113; A61B 5/1519; A61B 5/1513; A61B 5/15144; A61B 5/1411; A61B 5/150648; A61B 5/150656; A61B 5/150679; A61B 5/150687

See application file for complete search history.

(56) References Cited

U.S. PATENT DOCUMENTS

| | | | |
|---|---|---|---|
| 8,021,382 B2 | 9/2011 | Shi | |
| 2008/0039886 A1* | 2/2008 | Shi | A61B 5/15142 606/182 |
| 2008/0243161 A1* | 10/2008 | Abulhaj | A61B 5/15117 606/182 |

FOREIGN PATENT DOCUMENTS

| | | | |
|---|---|---|---|
| CN | 102379704 A | 3/2012 | |
| CN | 202568269 U | 12/2012 | |
| CN | 105816188 A | 8/2016 | |
| CN | 205597933 U | 9/2016 | |
| JP | 2005-021291 A | 1/2005 | |
| JP | 2005-034500 A | 2/2005 | |
| JP | 2010-246945 A | 11/2010 | |

* cited by examiner

DISPOSAL PUNCTURE DEPTH ADJUSTABLE SAFETY LANCET

TECHNICAL FIELD

The present invention relates to the medical lancing device field, especially an improved disposable puncture depth adjustable safety lancet. The present invention makes improvement of the previous disposable puncture depth adjustable safety lancet to overcome the risk of false triggering during the use of previous product. The lancet could adjust the puncture depth into the skin to meet the demands of different ages and different types of skin.

BACKGROUND OF INVENTION

Among the blood collection devices, the puncture depth adjustable safety lancet changes the disadvantage that the puncture depth of previous lancet could not change the puncture depth, so its application is wider and more adaptable. It could treat and different blood collection objects, such as the adult, children, male, female and different skin types separately and flexibly to achieve the optimal blood collection result. Therefore, this lancet has been well received by the medical staff and has been popular with the blood collection patients.

Chinese patent CN200945164Y (patent number: 200620077771.1) discloses and authorizes the utility model patent with the title of "A disposable puncture depth adjustable safety lancet". This patent mainly consists of two parts of triggering structure and adjusting head, wherein the adjusting head is located in the head of trigger and connected in a rotational way, and the adjusting head has a external end face with the needle hole at the front end and the needle hole has an inner end face at the rear end, and the inner end face is the rotating bevel or rotating step face to change the rotation angle of the adjusting head; and the rotating bevel or rotating step face meets the collision face of lancet core at the different depth of needle hole. The technical solution of this patent has been applied for many years and has achieved the good social and economic benefits, but it has the following deficiency in the practical applications: when the adjusting head is rotated to adjust the puncture depth during the use, it's liable to trigger the ejection structure by pressing the adjusting head by mistake to trigger the lancet earlier and cause the waste of lancets, as the adjusting head is connected to the trigger. Therefore, the subject of the present invention is how to solve the above problem in a better and effective way.

DISCLOSURE OF THE INVENTION

In view of the deficiency of the prior art, the present invention provides an improved disposable puncture depth adjustable safety lancet, which is to solve the problem of false triggering and waste of products during rotating the adjusting head.

In order to achieve the above purpose, the technical solution adopted by the present invention is: an improved disposable puncture depth adjustable safety lancet consists of a shell, a lancet core, a spring and a trigger.

The shell is fixedly at least two flexible claws and all flexible claws form a flexible clamp;

The lancet core is held in the flexible clamp and the spring pushes the tail of lancet core and acts on the ejecting direction of lancet core. The flexible clamp uses the hook at the end and clamping force to clamp the lancet core to be in locking state before triggering.

The head of trigger extends out of the front end of shell; the body of trigger is slideably connected in the shell; and the trigger is equipped with the bevel forcing the end of flexible clamp to stretch to the side direction in relative to the flexible claw;

The innovation is: under the assembly state, the shell is provided with an adjusting ring to adjust the puncture depth in the front end, and the adjusting ring is a cylindrical-shape component; the adjusting ring is sleeved at the outside of the trigger head and it's clearance fit with the trigger, and the end face of the trigger head to contact the skin is exposed out of the port at the frond end of the adjusting ring; the adjusting ring and the shell are connected in a rotational way in the peripheral direction of the lancet core, and the adjusting ring and the shell are connected in a fixed way in the axial direction of the lancet core, and a rotational locating structure is set between the adjusting ring and the shell in the rotation direction.

The adjusting ring is provided with the inner end face on the inner wall, and the inner end face faces the rear end direction of adjusting ring, and the inner end face is the rotating step face or rotating bevel, and the lancet core is provided with the side wing in relative to the rotating step face or rotating bevel, the end face of side wing facing the rotating step face or rotating bevel is the collision face, and the trigger is provided with the guide slot in relative to the side wing, and the guide slot is provided with an opening at the outside of trigger head, so that the collision face could rush to the rotating step face or rotating bevel through the opening during the ejection of lancet core; the rotation of adjusting ring could locate the adjusting ring in different locating positions at the peripheral direction of the shell, and the rotating step face or rotating bevel meets the collision face of lancet core in the different axial positions, thereby changing the puncture depth of needle tip.

The above described technical solution and the change are explained as follows:

1. In above described technical solution, the basic structure and the function of the "shell", "lancet core", "spring" and "trigger" are the prior art. Please refer to the technical solution cited in the background technology of present invention.

2. In above described technical solution, the "bevel" includes the flat face, cambered face or tapered face, but it's always set obliquely in relative to the axis of lancing device to constitute a bevel. In other words, the bevel has four types: the bevel in the form of flat face, the bevel in the form of concave surface (the bevel is straight in the oblique direction, and it's the concave surface or convex surface in the vertical direction, but its substantially bevel), the bevel in the form of tapered face and the bevel in the form of cambered face (the bevel has the concave arc or convex arc in the oblique direction, but it's substantially bevel). In the present invention, any type is applicable and it could be determined according to the practical situation.

The first type is the bevel in the form of flat face; the second type is the bevel in the form of concave surface; the third type is the bevel in the form of tapered face; and the fourth type is the bevel in the form of cambered face.

3. In above described technical solution, "the adjusting ring and the shell are connected in a rotational way in the peripheral direction of the lancet core, and the adjusting ring and the shell are connected in a fixed way in the axial direction of the lancet core" has many implementation forms, and it could achieve the purpose of present invention as long as it realizes the rotational connection of adjusting ring and shell in the peripheral direction and realizes the fixed connection in the axial direction.

4. In above described technical solution, the rotational locating structure is composed of the fitting of locating slots set apart in the peripheral direction and the convex, and one of the locating slot and convex is set on the fitting surface on the shell, and the other is set on the fitting surface of the adjusting ring. Two to six locating slots are set apart in the peripheral direction to constitute two to six gears of puncture depth for adjustment. In order to identify the adjusting gears, the adjusting ring is equipped with the corresponding gear marks at its outside and the shell is provided with the locating marks in relative to the gear marks for the two to six gears of puncture depths.

5. The disposable lancet of present invention consists of two structures of twist cap and cover cap. That is, the disposable lancet is usually designed with the protection cap, and the structure of protection cap could be the twist cap type or cover cap type. This doesn't affect the realization of the purpose of present invention.

The design principle and effect of the present invention are: In order to solve the problem of false triggering and waste of products during rotating the adjusting head, the head of lancet is designed with an adjusting ring to adjust the puncture depth, the adjusting ring is sleeved at the outside of the trigger head and it's clearance fit with the trigger, the adjusting ring and the shell are connected in a rotational way at the peripheral direction and connected in a fixed way in the axial direction, the adjusting ring realizes the gear switch through the rotating locating structure; when the rotation of adjusting ring makes the adjusting ring to locate in the different locating positions in relative to the shell in the peripheral direction through the fitting of the rotating step face or rotating bevel on the inner side and the collision face on the lancet core, the rotating step face or rotating bevel meets the collision face of lancet core at the different positions in the axial direction to change the puncture depth of the needle tip.

The present invention changes the original way of connecting the adjusting component to the trigger to the way of connecting the adjusting component to the shell, therefore the false triggering will not be caused as the rotation of the adjusting component is irrelevant to the trigger. The change of the connection relationship of adjusting component essentially and fundamentally solves the problem of product waste caused by the false triggering prone to happen during the rotation of adjusting head before. It appears that the present invention only changes the connection relationship between the adjusting component and the trigger, but it's not easy to think of the this lancet structure because: firstly, it's not easy to find the problem itself; secondly, the additional component can't be added; thirdly, with the change of the connection relationship of the adjusting component, the rotating step face or rotating bevel on the adjusting component is changed from the inner side of the trigger head to the outer side of the trigger head, so it's one difficult problem on how to make the lancet core on the inner side of the trigger to collide the rotating step face or rotating bevel on the outer side of the trigger during the ejection process; fourthly, how to realize the effective change of the connection relationship of the adjusting component. These factors are designed reasonably with simple structure and clever idea, and its not obvious for those of ordinary skill in the art, thus it has the outstanding and substantive features and significant progress.

The number description of above described drawings is as follows:

1. Shell; 2. Tail cover; 3. Lancet core; 4. Spring; 5. Trigger; 6. Twist cap; 7. Flexible claw; 8. Bevel; 9. Hook; 10. Adjusting ring; 11. End face; 12. Rotating step face; 13. Collision face; 14. Protruding rib; 15 Notch; 16. External locking gear; 17. Locating slot; 18. Convex; 19. Concave notch; 20. Connecting rod; 21. Convex curved edge; 22. Side wing; 23. Guide slot; 24. Opening; 25. Gear mark; 26. Locating mark.

SPECIFIC EMBODIMENT

With reference to the accompanying drawings and embodiment, the present invention will be described in detail.

Embodiment: An Improved Disposable Puncture Depth Adjustable Safety Lancet

Figure 1:
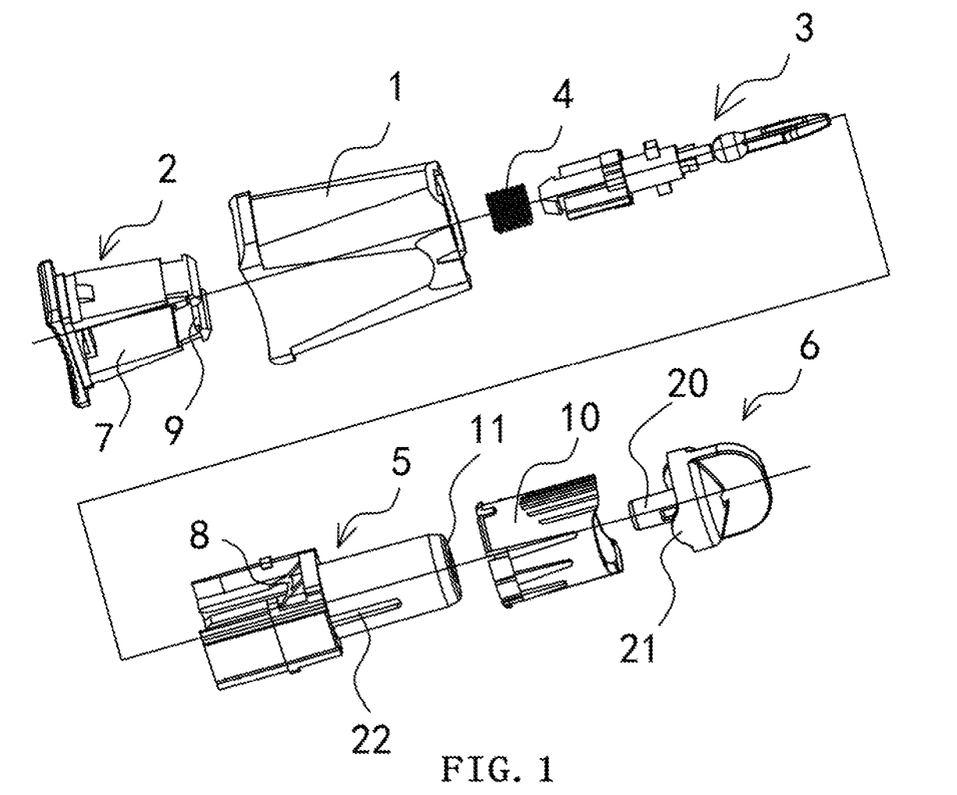
FIG. 1 is the exploded perspective view of lancet of the embodiment of present invention.
Figure 2:
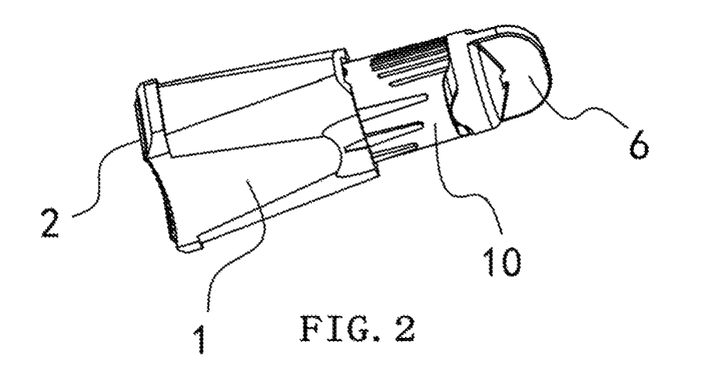
FIG. 2 is the perspective view of the lancet of the embodiment of present invention.
Figure 3:
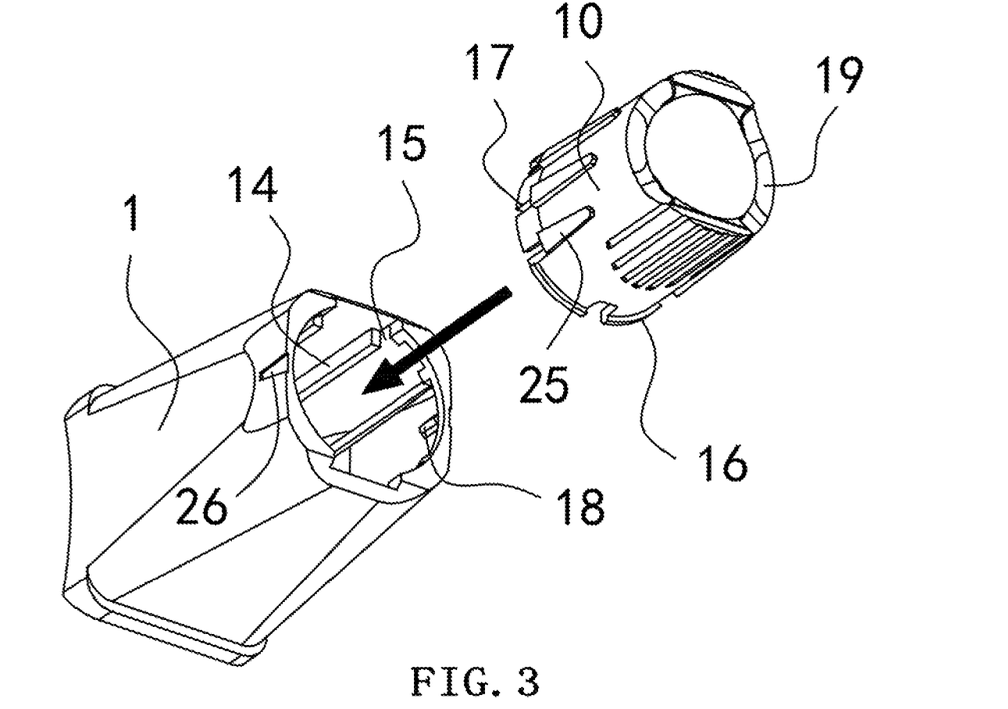
FIG. 3 is the schematic view of the assembly relationship between the adjusting ring and shell of the embodiment of present invention.
Figure 4:
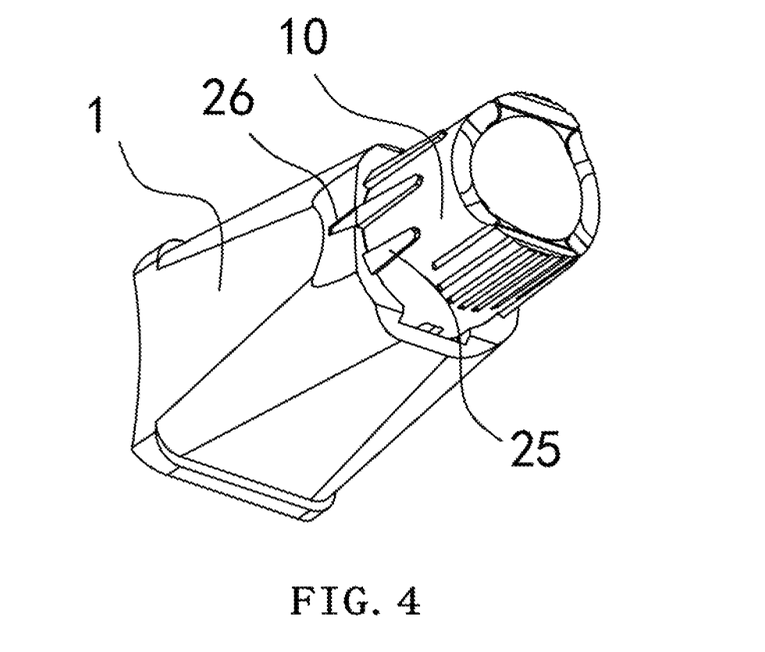
FIG. 4 is the view showing the assembly state of the adjusting ring and shell of the embodiment of present invention.

As shown in FIG. 1-7, the improved disposable puncture depth adjustable safety lancet consists of a shell 1, a tail cover 2, a lancet core 3, a spring, a trigger 5, a adjusting ring 10 and a twist cap 6 (see FIG. 1).

Under the assembly state (see FIG. 2), the tail cover 2 is covered at the rear end of the shell 1, and the tail cover 2 protrudes two flexible claws 7 in the symmetrical arrangement inside the shell 1 (see FIG. 1) and the two flexible claws 7 form a flexible clamp. The lancet core 3 is held in the flexible clamp and the spring 4 pushes the tail of lancet core 3 and acts on the ejecting direction of lancet core 3. The flexible clamp uses the hook 9 at the end (see FIG. 1) and clamping force to clamp the lancet core 3 to be in locking state before triggering. The head of trigger 5 extends out of the front end of shell 1; the body of trigger 5 is slideably connected in the shell 1; and the trigger 5 is equipped with the bevel 8 forcing the end of flexible clamp to stretch to the side direction in relative to the flexible claw 7 (see FIG. 6); The twist cap 6 is installed in the head of lancet.

Figure 5:
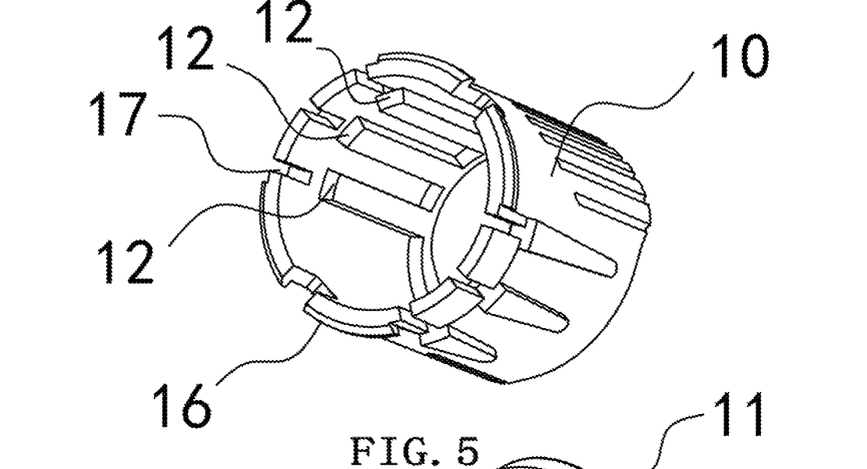
FIG. 5 is the perspective view of the adjusting ring of the embodiment of present invention.
Figure 6:
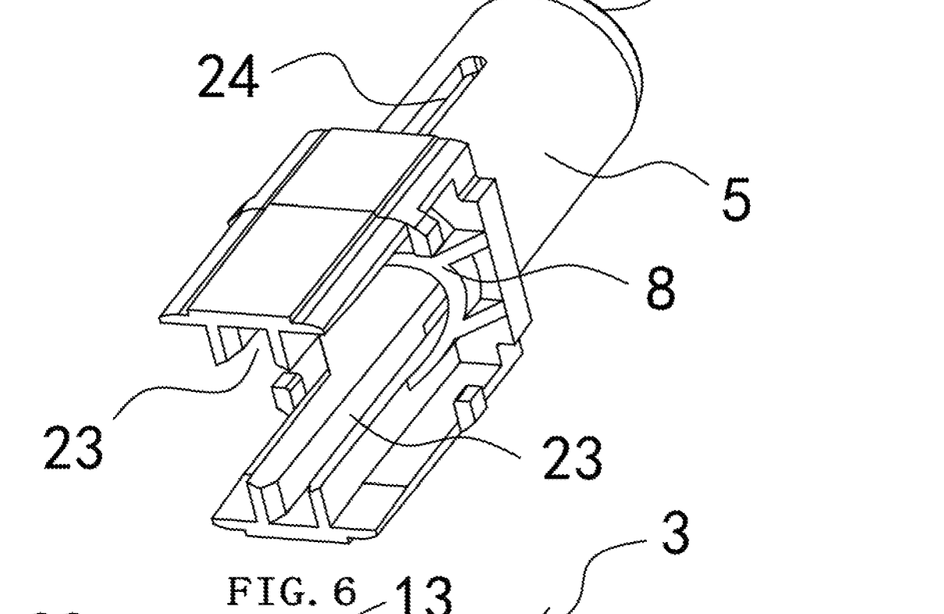
FIG. 6 is perspective view of the trigger of the embodiment of present invention.
Figure 7:
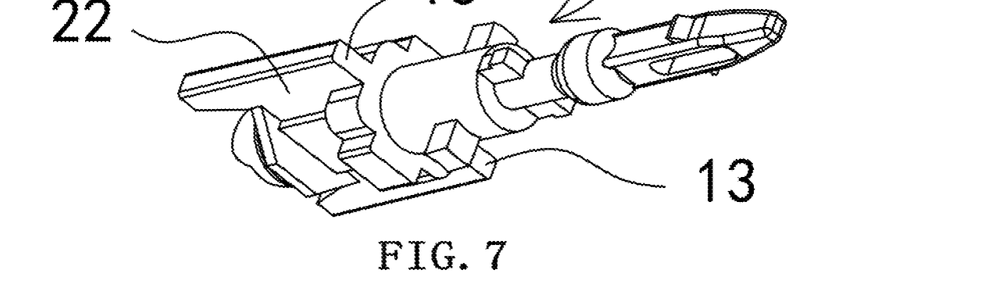
FIG. 7 is the perspective view of the lancet core of the embodiment of present invention.

The above content of the present invention is the prior art and the innovation of present invention lies in: under the assembly state, the adjusting ring 10 to adjust the puncture depth is set in the front end of the shell 1 and the adjusting ring 10 is a cylindrical-shape component (see FIG. 5). The adjusting ring 10 is sleeved at the outside of the trigger 5 head and it's clearance fit with the trigger 5, and the end face 11 (see FIG. 1) of the trigger 5 head to contact the skin is exposed out of the port at the frond end of the adjusting ring 10. The adjusting ring 10 and the shell 1 are connected in a rotational way in the peripheral direction of the lancet core 3, and the adjusting ring 10 and the shell 1 are connected in a fixed way in the axial direction of the lancet core 3, and a rotational locating structure is set between the adjusting ring 10 and the shell 1 in the rotation direction.

The adjusting ring 10 and the shell 1 are connected in a rotational way in the peripheral direction of the lancet core 3, and the adjusting ring 10 and the shell 1 are connected in a fixed way in the axial direction of the lancet core 3, and the specific implementation form is: the shell 1 is equipped with the protruding ribs 14 in the peripheral direction (see FIG. 3) and the protruding rib 14 is equipped with a notch 15 and all notches 15 in the peripheral direction are in the same peripheral direction, thus forming the discontinuous inner slots. And the adjusting ring 10 is equipped with the flanging extending outwards in relative to the discontinuous inner slots and the flanging sets and forms the external locking gears 16 at interval (see FIG. 3) in the peripheral direction of the adjusting ring 10. Under the assembly state (see FIGS. 3 and 4), the rear end of the adjusting ring 10 is inserted into the front end of the shell 1, and the external locking gears 16 are clamped into the discontinuous inner slots, so that the adjusting ring 10 and the shell 1 form the rotational connection in the peripheral direction of the lancet core 3 and form the fixed connection in the axial direction of the lancet core 3.

The rotational locating structure is composed of the fitting of locating slots 17 set apart in the peripheral direction and the convex 18, and one of the locating slot 17 and convex 18 is set on the fitting surface on the shell 1, and the other is set on the fitting surface of the adjusting ring 10. In this embodiment, the locating slot 17 is set at the outside peripheral surface of the adjusting ring 10 (see FIG. 3) and the convex 18 is set at the inside surface of the shell 1 (see FIG. 3). Two to six locating slots are set apart in the peripheral direction to constitute two to six gears of puncture depth for adjustment. In this embodiment, three locating slots 17 are set to form 3 gears of puncture depth for adjustment. The adjusting ring 10 is equipped with the corresponding gear marks 25 at its outside and the shell 1 is provided with the locating marks 26 in relative to the gear marks for three gears of puncture depths.

The adjusting ring 10 is provided with the inner end face on the inner wall, and the inner end face faces the rear end direction of adjusting ring 10, and the inner end face is the rotating step face 12, and the lancet core 3 is provided with the side wing 22 in relative to the rotating step face 12 (see FIG. 7), the end face of side wing 22 facing the rotating step face 12 is the collision face 13 (see FIG. 7), and the trigger 5 is provided with the guide slot 23 in relative to the side wing 22 (see FIG. 6), and the guide slot 23 is provided with an opening 24 at the outside of trigger 5 head (see FIG. 6), so that the collision face 13 could rush to the rotating step face 12 through the opening 24 during the ejection of lancet core 3. The rotation of adjusting ring 10 could locate the adjusting ring 10 in different locating positions at the peripheral direction of the shell 1, and the rotating step face 12 meets the collision face 13 of lancet core 3 in the different axial positions, thereby changing the puncture depth of needle tip.

The rotating step face 12 on the inner wall of the adjusting ring 10 consists of the left half section and right half section, and the left half section rotates along the adjusting ring 10 by 180° to overlap with the right half section. The collision face 13 of the lancet core 3 is bilaterally symmetrically arranged based on the axis of the lancet core 3, and the bilaterally symmetrical collision face 13 fits with the left half section and right half section of rotating step face 12.

The port at the front end of the adjusting ring 10 is laterally projected to be a concave notch 19 and the end face of the trigger 5 head to contact the skin is exposed from the concave notch 19, the twist cap 6 is located at the front end of the adjusting ring 10 and the twist cap 6 is equipped with the connecting rod 20 and convex curved edge 21. Under the assembly state, the end of connecting rod 20 is fitted with the head of lancet core 3, and the convex curved edge 21 of the twist cap 6 is fitted with the concave notch 19 of the adjusting ring 10, thus forming the rotational unplugging structure of the twist cap 6.

The operation process of the embodiment of the present invention is as follows:

Firstly, twist the protection cap.

Figure 8:
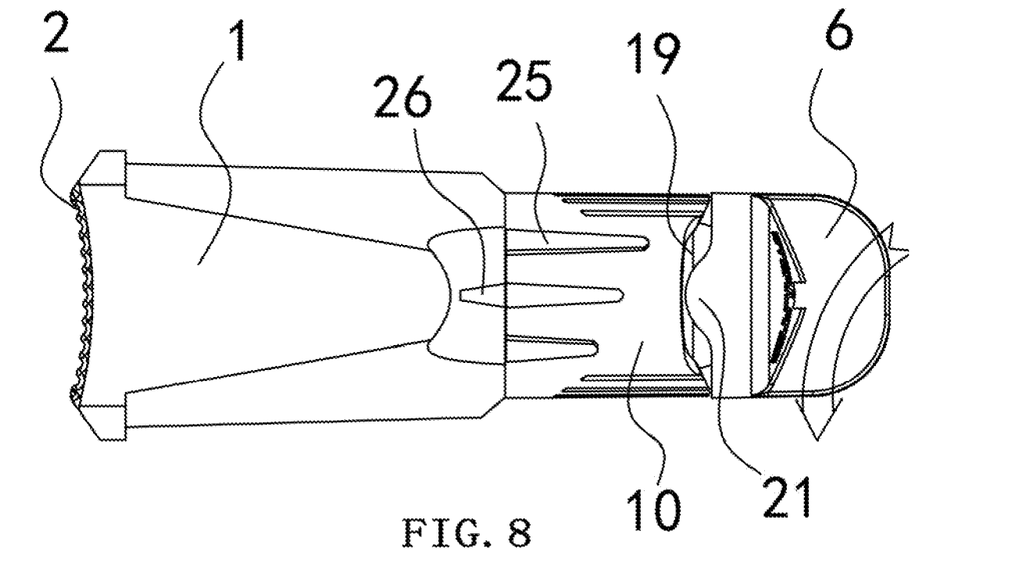
FIGS. 8 and 9 are the view showing the use state (1) of the embodiment of present invention.
Figure 9:
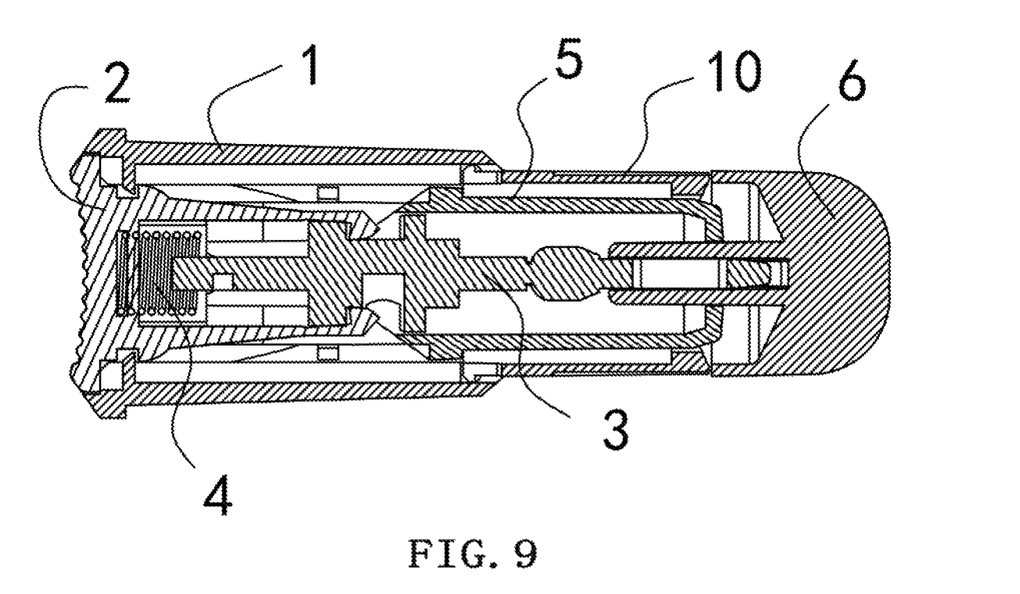

As shown in FIGS. 8 and 9, twist the twist cap 6 first. As the convex curved edge 21 of the twist cap 6 is rotationally fitted with the concave notch 19 of the adjusting ring 10, the connecting rod 20 of the lancet core 3 drives the protection bar of the lancet core 3 to rotate and finally break the neck between the protection bar and the body, then unplug the twist cap 6.

Secondly, adjust the puncture depth.

Figure 10:
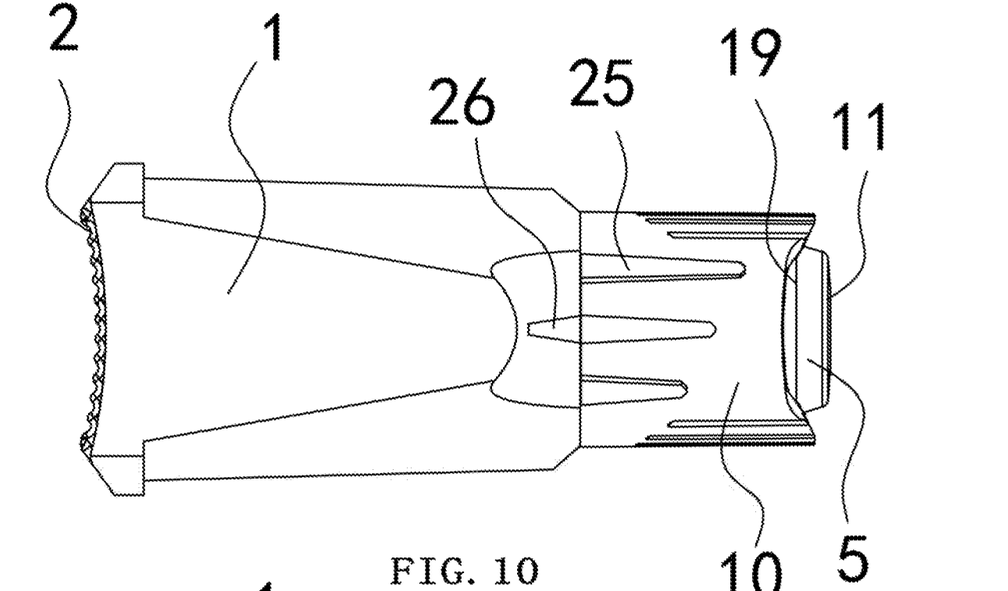
FIGS. 10 and 11 are the view showing the use state (2) of the embodiment of present invention.
Figure 11:
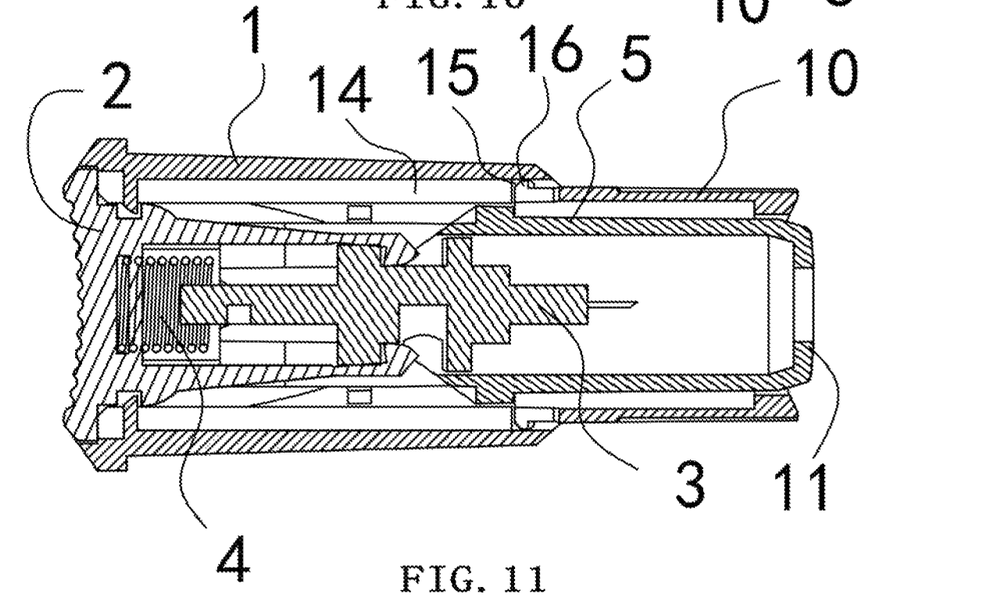

As shown in the FIGS. 10 and 11, rotate the adjusting ring 10 to make the adjusting ring 10 rotate in relative to the shell 1. Due to the function of the rotational locating structure between the adjusting ring 10 and the shell 1, the adjusting ring 10 is located at one angular position in relative to the shell 1, i.e. at one gear. At the same time, the rotating step face 12 on the inner wall of the adjusting ring 10 rotates with the adjusting ring 10 and finally makes the rotating step face 12 meet the collision face 13 of the lancet core 3 in the different axial position, thus changing the puncture depth of the needle tip.

Thirdly, press the trigger at the blood collection position

Figure 12:
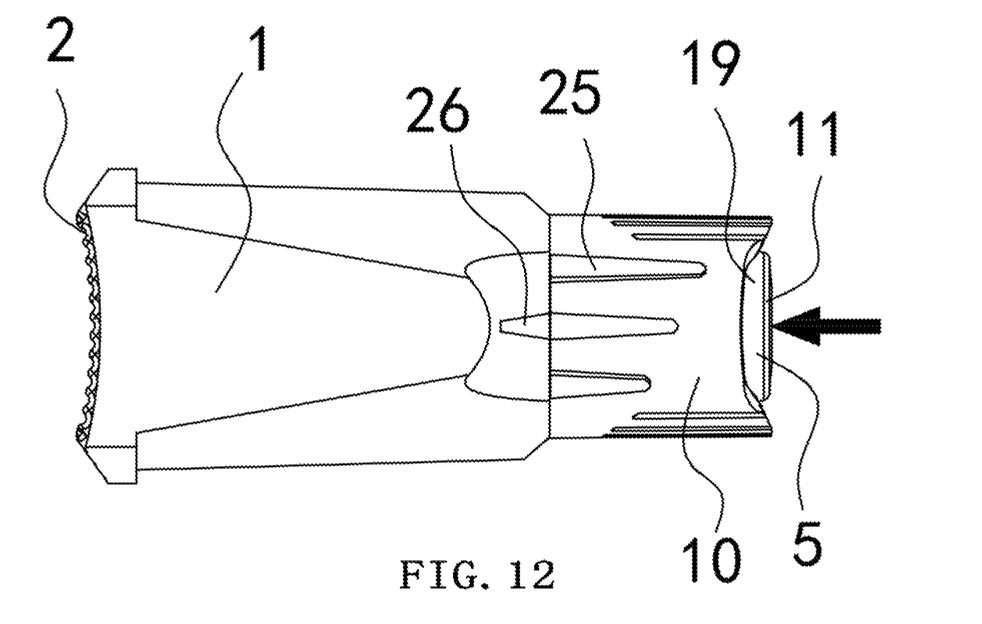
FIGS. 12 and 13 are the view showing the use state (3) of the embodiment of present invention.
Figure 13:
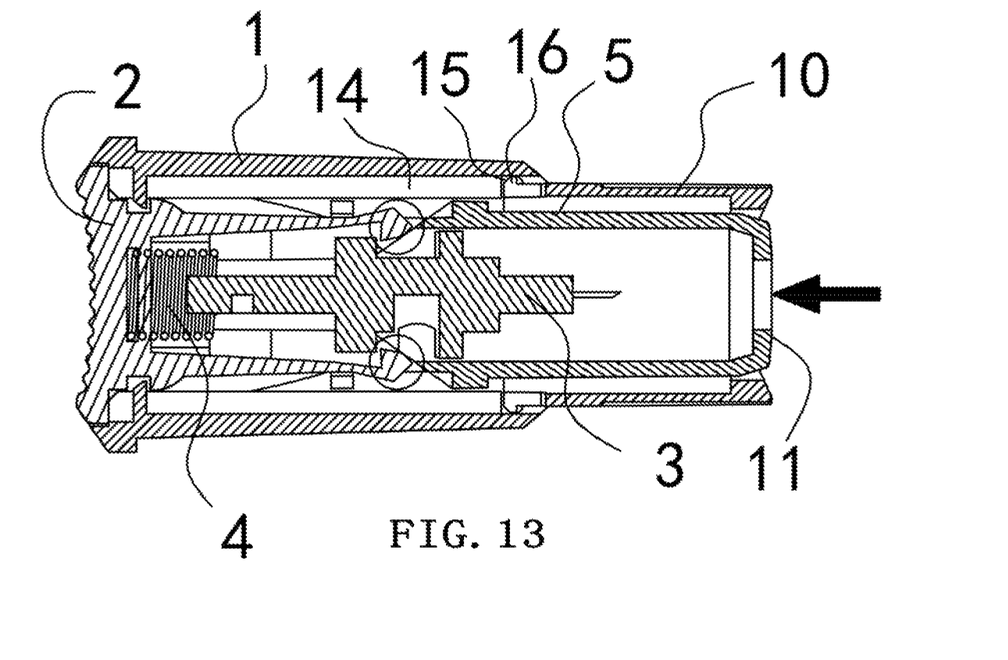

As shown in FIGS. 12 and 13, align the trigger 5 head with the blood collection position for pressing and when the trigger 5 head is pressed, the trigger 5 move backwards in relative to the shell 1, and the bevel 8 on the trigger 5 forces the flexible claws 7 to open laterally (see the two circles in FIG. 13) until they are near the unhooking point.

Fourthly, shoot and puncture.

Figure 14:
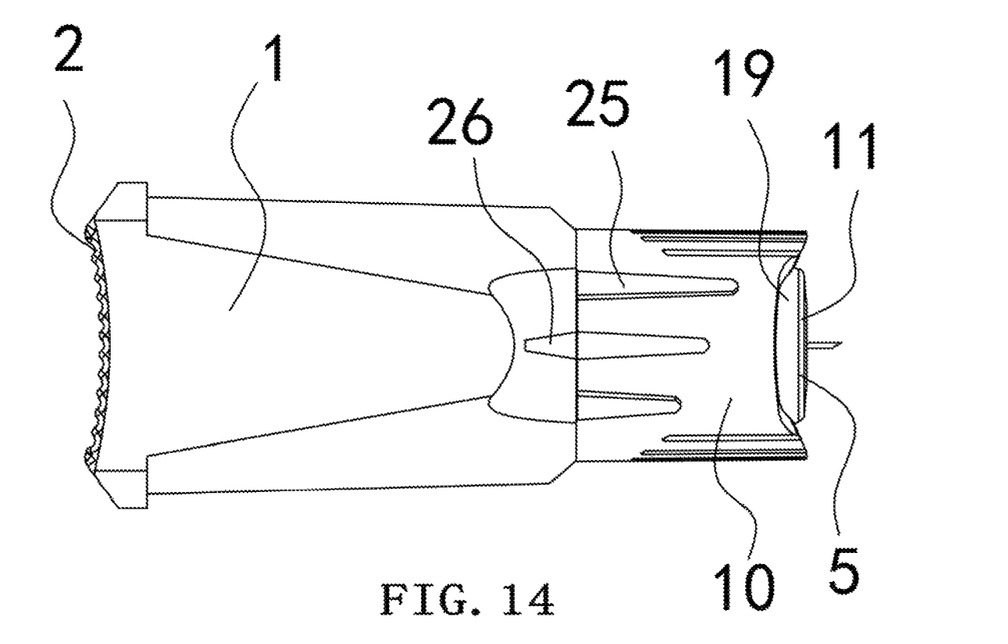
FIGS. 14 and 15 are the view showing the use state (4) of the embodiment of present invention.
Figure 15:
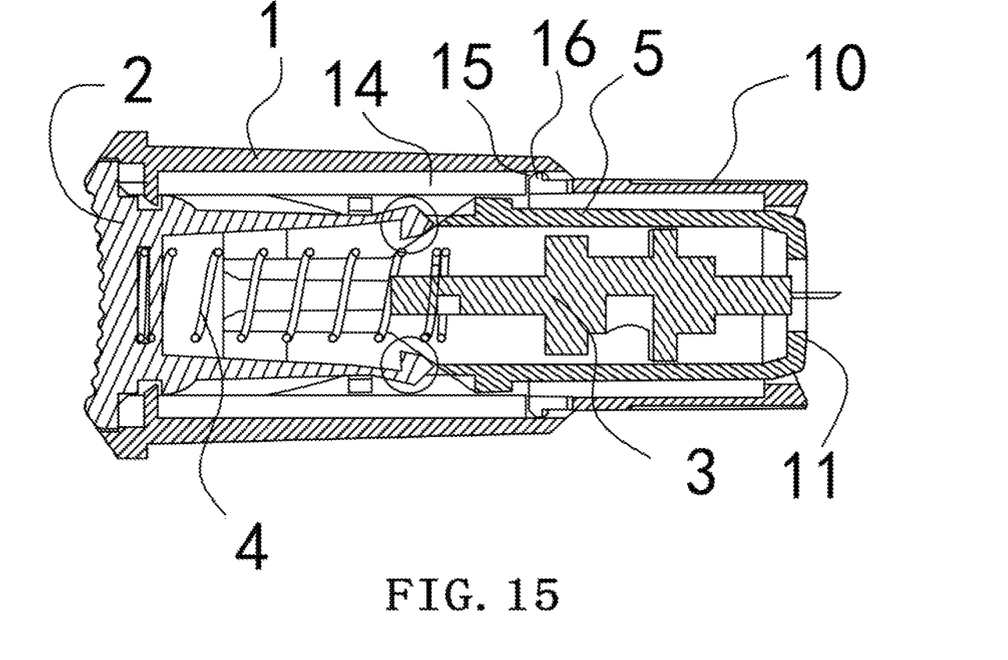

As shown in FIGS. 14 and 15, when the pressing exceeds the unhooking points, it triggers the unhooking of the lancet core 3 (see the two circles in FIG. 15) and enters the shooting and puncturing state under the pushing of the spring 4 to start the shooting and puncturing.

The following the description about the other embodiments and changes of the present invention:

1. The embodiment of the present invention is the twist cap type head pressing disposal lancet structure, and it is apparent to those skilled in the art after reading this disclosure that the present invention is equally applicable to the cover cap type head pressing disposal lancet structure.

2. In the above embodiment, the bevel 8 set on the trigger 5 is the flat face. The present invention actually has four types: the first type is the bevel in the form of flat face; the second type is the bevel in the form of concave surface (the bevel is straight in the oblique direction, and it's the concave surface or convex surface in the vertical direction, but its substantially bevel); the third type is the bevel in the form of tapered face; the fourth type is the bevel in the form of cambered face (the bevel has the concave arc or convex arc in the oblique direction, but it's substantially bevel). It could be determined according to the actual condition.

3. In the above embodiment, one flexible clamp formed by the two flexible claws 7, and it's the extension structure extended from the inner end face of the tail cover 2. But the present invention is not limited to this, as the flexible clamps could directly extend from the shell 1. For example, the shell 1 could be designed to be combined by the upper half section and lower half section, and one flexible claw could extend from one half section each, and after the combination of two half sections of the shell, two flexible claws could form a flexible clamp. At this time, the tail cover 2 could be omitted and integrated into the shell of two half sections. Therefore, the tail cover 2 and the flexible claw structure extended from the tail cover 2 are not deemed as the necessary condition in the claim 1, which could be understood and recognized by those skilled in the art.

4. In the above embodiment, the flexible clamp is formed by two symmetrically arranged flexible claws. But the number of flexible claws in the present invention is not limited to two, and it could contain more than two claws, such as three, four, and five, etc. These flexible claws could be arranged around the lancet core to reach the purpose of the present invention and realize the same technical effect. This is the change that could be easily understood by those skilled in the art.

5. In the above embodiment, the rotating step face 12 is set on the inner wall of the adjusting ring 10 to realize several puncture depths and actually when the rotating step face 12 is changed to the rotating bevel to reach the purpose of the present invention and realize the same technical effect, which is the change that could be easily understood by those skilled in the art.

6. In the above embodiment, it describes one specific implementation form for the rotational connection of the adjusting ring 10 and the shell 1 in the peripheral direction and the fixed connection in the axial direction, but the present invention is not limited to this, and it could also have the following forms:

(1) The shell 1 is provided with the ring-type inner slots on the inner wall in the peripheral direction. And the adjusting ring 10 is equipped with the flanging extending outwards in relative to the ring-type inner slots and the flanging sets and forms the external locking gears 16 at interval in the peripheral direction of the adjusting ring 10. Under the assembly state, the rear end of the adjusting ring 10 is inserted into the front end of the shell 1, and the external locking gears 16 are clamped into the ring-type inner slots, so that the adjusting ring 10 and the shell 1 form the rotational connection in the peripheral direction of the lancet core 3 and form the fixed connection in the axial direction of the lancet core 3.

(2) The shell 1 is provided with the ring-type outer slots on the outer wall in the peripheral direction. And the adjusting ring 10 is equipped with the flanging extending inwards in relative to the outer inner slots and the flanging sets and forms the internal locking gears at interval in the peripheral direction of the adjusting ring 10. Under the assembly state, the rear end of the adjusting ring 10 is inserted into the front end of the shell 1, and the internal locking gears are clamped into the ring-type outer slots, so that the adjusting ring 10 and the shell 1 form the rotational connection in the peripheral direction of the lancet core 3 and form the fixed connection in the axial direction of the lancet core 3.

(3) Combining the above two forms to obtain the third form. And so forth.

In summary, as along as the adjusting ring 10 and the shell 1 have the rotational connection relationship in the peripheral direction and have the fixed connection relationship in the axial direction at the same time in the present invention, if could reach the purpose of the present invention and get the same effect.

7. In the above embodiment, the concave notch 19 is set on the adjusting ring 10 and the convex curved edge is set on the twist cap 6. Actually, setting the convex curved edge 21 on the adjusting ring 10 and setting the concave notch 19 on the twist cap 6 could also reach the purpose of the present invention and realize the same technical effect, which is the change that could be easily understood by those skilled in the art.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A disposable puncture-depth-adjustable safety lancet comprising:
a shell fixed to at least two flexible claws that form a flexible clamp having an end with a hook;
a lancet core configured to be held in the flexible clamp, the flexible clamp being configured to use the hook and a clamping force to clamp the lancet core in a locking state before triggering of the safety lancet;
a spring configured to push against a tail of the lancet core in an ejecting direction of the lancet core; and
a trigger having (i) a head that extends out of a front end of the shell, (ii) a body that is slideably connected to the shell, and (iii) a bevel configured to force the end of the flexible clamp to stretch in side directions corresponding to each of the at least two flexible claws, wherein, in an assembled state:
a cylindrical-shaped adjusting ring is provided at the front end of the shell to adjust a puncture depth of a needle tip;
the adjusting ring is sleeved at an outside of the trigger head and is clearance fit with the trigger;
an end face of the trigger head configured to contact skin extends out of a port at a front end of the adjusting ring;
the adjusting ring and the shell are connected to form (i) a rotational connection in a peripheral direction of the lancet core and (ii) a fixed connection in an axial direction of the lancet core;
a rotational locating structure is formed by the adjusting ring and the shell in a peripheral direction of the shell;
the adjusting ring has an inner wall with an inner end face that (i) faces a rear end direction of the adjusting ring and (ii) is a rotating step face or rotating bevel;
the lancet core has a side wing positioned relative to the rotating step face or rotating bevel, and an end face of the side wing facing the rotating step face or rotating bevel is a collision face;
the trigger has a guide slot that is positioned relative to the side wing, the guide slot being provided with an opening at the outside of the trigger head so that the collision face can move toward the rotating step face or rotating bevel through the opening during ejection of the lancet core;

rotating the adjusting ring locates the adjusting ring in different locating positions in the peripheral direction of the shell; and the rotating step face or rotating bevel is configured to meet the collision face of the lancet core at different axial positions, thereby changing the puncture depth of the needle tip.

2. The lancet as claimed in claim 1, wherein:

the shell is equipped with protruding ribs in the peripheral direction of the shell, each of the protruding ribs being equipped with a notch, and all of the notches being aligned in the same peripheral direction, thereby forming discontinuous inner slots; and the adjusting ring is equipped with flanging extending outwards relative to the discontinuous inner slots and the flanging forms external locking gears at intervals in a peripheral direction of the adjusting ring; and in the assembled state, a rear end of the adjusting ring is inserted into the front end of the shell, and the external locking gears are clamped into the discontinuous inner slots, so that the adjusting ring and the shell form the rotational connection in the peripheral direction of the lancet core and form the fixed connection in the axial direction of the lancet core.

3. The lancet as claimed in claim 1, wherein:

the shell has an inner wall equipped with ring-type inner slots in the peripheral direction of the shell;

the adjusting ring is equipped with flanging extending outwards relative to the ring-type inner slots; and the flanging forms external locking gears at intervals in a peripheral direction of the adjusting ring; and in the assembled state, a rear end of the adjusting ring is inserted into the front end of the shell, and the external locking gears are clamped into the ring-type inner slots, so that the adjusting ring and the shell form the rotational connection in the peripheral direction of the lancet core and form the fixed connection in the axial direction of the lancet core.

4. The lancet as claimed in claim 1, wherein:

the shell has an outer wall equipped with ring-type outer slots in the peripheral direction of the shell;

the adjusting ring is equipped with flanging extending inwards relative to the ring-type outer slots; and the flanging forms internal locking gears at intervals in a peripheral direction of the adjusting ring; and in the assembled state, a rear end of the adjusting ring is inserted into the front end of the shell, and the internal locking gears are clamped into the ring-type outer slots, so that the adjusting ring and the shell form the rotational connection in the peripheral direction of the lancet core and form the fixed connection in the axial direction of the lancet core.

5. The lancet as claimed in claim 1, wherein:

the rotational locating structure is composed of a fitting of (i) locating slots set apart in the peripheral direction of the shell and (ii) a convex; and one of the locating slots and the convex is set on a fitting surface of the shell, and another of the locating slots and the convex is set on a fitting surface of the adjusting ring.

6. The lancet as claimed in claim 5, wherein:

two to six of the locating slots are set apart in the peripheral direction of the shell to constitute two to six gears of puncture depths for adjustment.

7. The lancet as claimed in claim 6, wherein:

the adjusting ring has an outside equipped with corresponding gear marks, and the shell is provided with locating marks positioned relative to the gear marks for the two to six gears of puncture depths.

8. The lancet as claimed in claim 1, wherein:

the rotating step face or rotating bevel on the inner wall of the adjusting ring comprises a left half section and a right half section, and the left half section rotates along the adjusting ring by 180° to overlap with the right half section;

the collision face of the lancet core is bilaterally symmetrically arranged around an axis of the lancet core; and the collision face fits with the left half section and right half section of the rotating step face or rotating bevel.

9. The lancet as claimed in claim 1, wherein:

the port at the front end of the adjusting ring is laterally projected to be a concave notch;

the end face of the trigger head configured to contact the skin is exposed from the concave notch;

a twist cap is located at the front end of the adjusting ring and is equipped with a connecting rod and a convex curved edge; and in the assembled state, an end of the connecting rod is fitted with a head of the lancet core, and the convex curved edge of the twist cap is fitted with the concave notch of the adjusting ring thereby forming a rotational unplugging structure of the twist cap.

* * * * *